United States Patent
Tomono et al.

(10) Patent No.: US 7,244,588 B2
(45) Date of Patent: Jul. 17, 2007

(54) COLD-INDUCED EXPRESSION VECTOR

(75) Inventors: Jun Tomono, Kusatsu (JP); Harumi Ueno, Kusatsu (JP); Masayuni Kishimoto, Otsu (JP); Hiroaki Sagawa, Kusatsu (JP); Ikunoshin Kato, Koka-gun (JP)

(73) Assignee: Takara Bio Inc., Shiga (JP)

( * ) Notice: Subject to any disclaimer, the term of this patent is extended or adjusted under 35 U.S.C. 154(b) by 10 days.

(21) Appl. No.: 10/538,793

(22) PCT Filed: Dec. 11, 2003

(86) PCT No.: PCT/JP03/15835

§ 371 (c)(1),
(2), (4) Date: Jun. 10, 2005

(87) PCT Pub. No.: WO2004/053126

PCT Pub. Date: Jun. 24, 2004

(65) Prior Publication Data

US 2006/0148033 A1 Jul. 6, 2006

(30) Foreign Application Priority Data

Dec. 11, 2002 (JP) .............................. 2002-359956

(51) Int. Cl.
C12N 15/00 (2006.01)
C12P 21/06 (2006.01)
C07K 1/00 (2006.01)

(52) U.S. Cl. .................. 435/69.1; 435/70.1; 435/91.4; 435/320.1

(58) Field of Classification Search ...................... None
See application file for complete search history.

(56) References Cited

U.S. PATENT DOCUMENTS 5,654,169 A 8/1997 Oppenheim et al.
6,479,260 B1 * 11/2002 Takayama et al. ......... 435/69.1
6,610,533 B1 * 8/2003 Inouye et al. ............ 435/320.1

FOREIGN PATENT DOCUMENTS

| EP | 1 033 408 A1 | 9/2000 |
|---|---|---|
| WO | WO 96/03521 | 2/1996 |
| WO | WO 98/27220 | 6/1998 |
| WO | WO 98/27220 A1 | 6/1998 |
| WO | WO 00/11148 A2 | 3/2000 |
| WO | WO 03/074657 A2 | 9/2003 |

OTHER PUBLICATIONS

Yamanaka et al (Mutation Analysis of the 5' Untranslated Region of the Cold Shock CspA mRNA of *Escherichia coli*. Journal of Bacteriology, 1999. 6284-62910).*
Yamanaka et al., Mutation analysis of the 5' untranslated region of the cold shock *cspA* mRNA of *Escherichia coli*, *Journal of Bacteriology*, 6284-6291 (Oct. 1999).
Vasina et al., Recombinant protein expression at low temperatures under the transcriptional control of the major *Escherichia coli* cold shock promoter *cspA*, *Applied and Environmental Microbiology*, 1444-1447 (Apr. 1996).
Xia et al., The cold box stem-loop proximal to the 5'-end of the *Escherichia coli cspA* gene stabilizes its mRNA at low temperatures, *The Journal of Biological Chemistry*, 6005-6011 (Feb. 2002).
Fang et al., Transcription of *cspA*, the gene for the major cold-shock protein of *Escherichia coli*, is negatively regulated at 37° C by the 5'-untranslated region of its mRNA, *FEMS Microbiology Letters* 176:39-43 (1999).
Wang et al., Cspl, the ninth member of the CapA family of *Escherichia coli*, is induced upon cold shock, *Journal of Bacteriology*, 1603-1609 (Mar. 1999).
Goldenberg et al., Role of *Escherichia coli cspA* promoter sequences and adaptation of translational apparatus in the cold shock response, *Mol. Gen. Genet.*, 256:282-290 (1997).
Wouters et al., Clustered organization and transcriptional analysis of a family of five *csp* genes of *Lactococcus lactis* MG1363, *Microbiology*, 144:2885-2893 (1998).
Jiang et al., The role of the 5'-end untranslated region of the mRNA for CspA, the major cold-shock protein of *Escherichia coli*, in cold-shock adaptation, *Journal of Bacteriology*, 4919-4925 (Aug. 1996).
Michael L. Sprengart et al., "The downstream box: an efficient and independent translation initiation signal in *Escherichia coli*", *The EMBO Journal*, vol. 15, No. 3, pp. 665-674, 1996.

* cited by examiner

*Primary Examiner*—David Guzo
*Assistant Examiner*—Kimberly A. Makar
(74) *Attorney, Agent, or Firm*—Browdy & Neimark, PLLC

(57) ABSTRACT

A vector having a region encoding a cold shock protein gene mRNA-origin 5'-nontranslated region, characterized in that the 5'-nontranslated region has a mutation having been transferred therein so as to change the distance of the stem structure formed by the region.

8 Claims, No Drawings

COLD-INDUCED EXPRESSION VECTOR

TECHNICAL FIELD

The present invention relates to a vector used for genetic engineering and a method for expressing proteins using said vector.

BACKGROUND ART

Techniques for production of useful proteins using genetic engineering are widely used nowadays. Among these, expression systems using *Escherichia coli* as a host are the most commonly used expression systems. Many proteins have been produced using recombinants. A so-called expression vector is generally constructed and used for the production of useful proteins using recombinants. In the expression vector, a gene of interest is placed under the control of a promoter which is recognized by an RNA polymerase. Exemplary promoters used for expression vectors for *Escherichia coli* as a host are lac, trp, tac, gal and ara promoters. Expression vectors that utilize promoters other than those directly recognized by *Escherichia coli* RNA polymerase include the pET-system (Novagen). The pET-system utilizes a promoter recognized by an RNA polymerase from bacteriophage T7 which infects *Escherichia coli* (see J. Mol. Biol., 189:113–130 (1986); Gene, 56:125–135 (1987)). In case of the pET-system, T7 RNA polymerase is expressed in *Escherichia coli*, a gene of interest placed downstream of T7 promoter in an expression vector is transcribed by T7 RNA polymerase, and the protein of interest is synthesized using the translation system of the host.

However, if a protein of interest is expressed at a high level using one of many *Escherichia coli* expression systems including the pET-system, the protein of interest may form an insoluble complex called inclusion body in many cases. As a result, the amount of the protein of interest in its active form is greatly reduced. It has been reported for several polypeptides that active polypeptides were obtain by solubilization and refolding of inclusion bodies. The recovery rates are generally low in many cases. In addition, appropriate refolding conditions need to be examined for each protein of interest. Thus, a system for directly expressing an active protein in *Escherichia coli* has been desired.

It is considered that inclusion bodies are formed as a result of the following. An intermediate of a translated polypeptide chain prior to folding into its proper conformation is interwound with another polypeptide chain due to intermolecular interaction to form a huge insoluble complex. In such a case, it is known that the expression level of a protein in its active form is increased by culturing recombinant *Escherichia coli* cells at a temperature lower than the conventional one 37° C. (20 to 30° C.). It is supposed that this is because the slow translation by ribosome provides a sufficient time for the intermediate to be folded into its proper structure, and the slow action of intracellular proteolytic enzyme under the low-temperature conditions increases the stability of expressed active protein. Thus, attention has been paid to a method in which recombinant *Escherichia coli* cells are cultured under low-temperature conditions as being useful for producing a protein that forms inclusion bodies.

If a culture temperature for *Escherichia coli* cells during the logarithmic growth phase is lowered from 37° C. to 10–20° C., growth of the *Escherichia coli* cells is temporarily arrested, during which expression of a group of proteins called cold shock proteins is induced. The proteins are classified based on the induction level into two groups: a group I (10-fold or more) and a group II (less than 10-fold). Proteins in the group I include CspA, CspB, CspG and CsdA (see J. Bacteriol., 178:4919–4925 (1996); J. Bacteriol., 178:2994–2997 (1996)). Since the expression level of CspA (WO 90/09447) reaches 13% of the total cellular protein 1.5 hours after temperature shift from 37° C. to 10° C. (see Proc. Natl. Acad. Sci. USA, 87:283–287 (1990)), attempts have been made to utilize the promoter for the cspA gene for production of a recombinant protein at a low temperature.

Regarding a system for expressing a recombinant protein under low-temperature conditions using the cspA gene, the following effectiveness has been shown in addition to the above-mentioned highly efficient transcription initiation by the promoter for the gene at a low temperature.

(1) If mRNA that is transcribed from the cspA gene and capable of being translated does not encode a functional CspA protein (specifically, if it encodes only a portion of the N-terminal sequence of the CspA protein), such mRNA inhibits expression of other *Escherichia coli* proteins including cold shock proteins for a long period of time. During this period, the mRNA is preferentially translated (J. Bacteriol., 178:4919–4925 (1996); WO 98/27220). This phenomenon is called LACE (low temperature-dependent antibiotic effect of truncated cspA expression) effect.

(2) A sequence consisting of 15 nucleotides called a downstream box is located 12 nucleotides downstream of the initiation codon of the cspA gene. The translation efficiency under low-temperature conditions is made high due to this sequence.

(3) A 5'-untranslated region consisting of 159 nucleotides is located between the transcription initiation site and the initiation codon in the mRNA for the cspA gene. This region has a negative effect on the expression of CspA at 37° C. and a positive effect under low-temperature conditions.

In particular, the phenomenon as described in (1) above suggests the feasibility of specific expression of only a protein of interest utilizing the cspA gene. Thus, it is expected that the system can be applied to production of highly pure recombinant proteins or preparation of isotope-labeled proteins for structural analyses.

It is known that it may be difficult to culture an *Escherichia coli* cell containing an expression vector to a level at which the cell can be subjected to induction, or even construction of an expression vector may be impossible if expression control of the promoter for the gene is incomplete and the gene product is harmful to the host (see, for example, U.S. Pat. No. 5,654,169).

Modification of the expression vector has been tried using the 5'-untranslated region of the cspA gene in order to solve the above-mentioned problems, to further increase the gene expression efficiency, and to readily obtain the expressed product (WO 99/27117). Modification by introducing an operator for making the expression control strict or by introducing a mutation into the 5'-untranslated region for increasing the gene expression level is disclosed therein.

DISCLOSURE OF INVENTION

As described above, the protein expression system under low-temperature conditions is considered to be a very effective system, and further improvements of expression efficiency and the like are desired.

The main object of the present invention is to construct a more excellent system for gene expression under low-temperature conditions, for example, by increasing gene expression efficiency of an expression vector utilizing a csp gene.

In order to achieve this object, the present inventors have assessed the effect of modification introduced into a nucleotide sequence of a 5'-untranslated region derived from a csp gene. As a result, the present inventors have found that adjustment of a distance between stems formed in a portion corresponding to the 5'-untranslated region of mRNA increases the expression level of a protein encoded by the downstream sequence. Furthermore, the present inventors have constructed a vector containing a DNA that encodes such a modified 5'-untranslated region. Thus, the present invention has been completed.

The present invention is outlined as follows. The first aspect of the present invention relates to a vector having a portion encoding a 5'-untranslated region derived from an mRNA for a cold shock protein gene, wherein a mutation is introduced into the 5'-untranslated region such that a distance between stem structures formed in said region is altered.

According to the first aspect, the mutation introduced into the 5'-untranslated region is exemplified by insertion or deletion of a nucleotide. A vector in which the mutation is introduced into a region of the *Escherichia coli* cspA gene corresponding to nucleotide 593 to nucleotide 598 in SEQ ID NO:1 exemplifies a particularly preferable embodiment.

In the vector according to the first aspect, the portion encoding a 5'-untranslated region may further have an operator. A 5'-untranslated region that has the nucleotide sequence of SEQ ID NO:2, 3 or 4 is a particularly preferable example of the 5'-untranslated region in the vector.

The vector of the first aspect may have a promoter located upstream of the portion encoding a 5'-untranslated region. In addition, it may have a nucleotide sequence that is complementary to an anti-downstream box sequence in a ribosormal RNA of a host to be used, wherein said nucleotide sequence is located downstream of the portion encoding a 5'-untranslated region.

For example, the vector of the first aspect may be a plasmid vector.

The second aspect of the present invention relates to a method for expressing a protein of interest, the method comprising:

(1) transforming a host with the vector of the first aspect into which a gene encoding a protein of interest has been incorporated to obtain a transformant;

(2) culturing the transformant; and (3) shifting the culture temperature down to one lower than a conventional temperature to express the protein of interest.

According to the second aspect, a promoter may be induced during or after step (3).

BEST MODE FOR CARRYING OUT THE INVENTION

Hereinafter, the present invention will be described in detail.

As used herein, "a region" refers to an area of a nucleic acid (DNA or RNA). As used herein, "a 5'-untranslated region of an mRNA" refers to a region that does not encode a protein, and is located on the 5' side of an mRNA synthesized as a result of transcription from a DNA. Hereinafter, the region may also be referred to as "a 5'-UTR (5'-Untranslated Region)". Unless otherwise noted, the 5'-UTR refers to the 5'-untranslated region of mRNA for the *Escherichia coli* cspA gene or a modification thereof.

As used herein, "a cold shock protein gene" refers to a gene encoding a protein whose expression is induced upon lowering the growth temperature of an organism from its physiological temperature.

A portion encoding a 5'-UTR of a cold shock protein mRNA used according to the present invention is a portion that encodes a region 5' to the initiation codon in the mRNA for the gene. Such a portion is characteristically found in an *Escherichia coli* cold shock protein gene (cspA, cspB, cspG, csdA or the like) (J. Bacteriol., 178:4919–4925 (1996); J. Bacteriol., 178:2994–2997 (1996)). A portion of 100 nucleotides or more from the 5' end in the mRNA transcribed from such a gene is not translated into a protein. This portion is important for cold response of gene expression. If this 5'-untranslated region is added to an mRNA for an arbitrary protein at its 5' end, translation from the mRNA into a protein takes place under low-temperature conditions.

"A 5'-untranslated region of an mRNA" used according to the present invention is not limited to one derived from the above-mentioned specific gene. A 5'-untranslated region that is derived from a cold shock protein gene and is capable of forming two or more stem structures can be used according to the present invention.

Portions encoding 5'-UTRs derived from the cold shock protein genes as listed above can be used for the vector of the present invention. In particular, one derived from the *Escherichia coli* cspA gene can be preferably used. The nucleotide sequence of the *Escherichia coli* cspA gene is registered and available to the public under accession no. M30139 from the GenBank gene database. The nucleotide sequence is shown in SEQ ID NO:1. Furthermore, a 5'-UTR in which the nucleotide sequence is partially modified can also be used according to the present invention. For example, one can use the 5'-UTR-encoding portion from the cspA gene contained in a plasmid pMM047 or pMM048 as described in WO 99/27117. The nucleotide sequence of the 5'UTR-encoding portion from the *Escherichia coli* cspA gene contained in the plasmid pMM048 is shown in SEQ ID NO:5. This sequence is identical to the nucleotide sequence of the portion encoding the 5'-UTR contained in the plasmid pCold08NC2 used in Examples in the present specification.

The present invention is characterized in that a mutation is introduced into a 5'-UTR-encoding portion such that the mutation adjusts a distance between stems which are secondary structures presumably formed in the 5'-UTR. For example, a distance between stems can be increased or decreased by inserting nucleotide(s) into a portion corresponding to a region between the stems or by deleting a part of nucleotides in such a portion. There is no specific limitation concerning the position at which a mutation is introduced, or the number of nucleotide(s) to be inserted or deleted in a mutation as long as the expression level of a downstream linked gene is elevated as a result of the mutation as compared with one without the mutation. It is needless to say that the mutation preferably does not interfere with the ability of the 5'-UTR to achieve cold-specific gene expression.

It is expected that the 5'-UTR derived from the *Escherichia coli* cspA gene forms stem structures in a region from nucleotide 584 to nucleotide 593 and a region from nucleotide 598 to nucleotide 608 in the nucleotide sequence of SEQ ID NO:1. Thus, the distance between the stems can be adjusted by introducing insertion or deletion of nucleotide(s) into a portion between the above-mentioned regions (from nucleotide 593 to nucleotide 598) or a portion corresponding to said portion in a 5'-UTR having an introduced mutation. The present invention is not limited to the above-mentioned adjustment of distance between stems.

The deletion mutations according to the present invention include deletion of one to all of nucleotides in a portion between stems. Insertion mutations are exemplified by insertion of 1 to 100 nucleotide(s), preferably 3 to 60 nucleotides, more preferably 8 to 40 nucleotides.

Although it is not intended to limit the present invention, the 5'-UTRs contained in the plasmid vectors described in Examples, pCold08s2, pCold08s12 and pCold08s32, exemplify preferred embodiments of the present invention. The nucleotide sequences of the 5'-UTRs contained in the plasmid vectors are shown in SEQ ID NOS:2, 3 and 4, respectively.

The expression vector of the present invention can be prepared using a portion encoding a 5'-UTR which is prepared according to the present invention and in which a distance between stems is adjusted as described above. Specifically, it may be prepared as follows. Secondary structures formed by an mRNA encoded by a 5'-UTR-encoding DNA as a starting material are assumed. An insertion or deletion mutation is introduced into a portion presumably corresponding to a portion between stems using a known method. The thus obtained DNA is incorporated into a vector along with an appropriate promoter.

The vector of the present invention may be any one of commonly used vectors (e.g., plasmid, phage or virus vectors) as long as it can be used to achieve the object as a vector. It does not create inconvenience if the vector of the present invention may be integrated into a genomic DNA in a host after transferred into the host.

The 5'-UTR is inserted between a promoter and a region encoding a protein of interest in the vector of the present invention. Examples of the promoters used according to the present invention include, but are not limited to, promoters derived from cold shock protein genes (e.g., cspA, cspB, cspG and cspA) which are expected to have high promoter activities at a low temperature. The promoter may be any one if it has an activity of initiating transcription into RNA in a host to be used. If *Escherichia coli* is to be used as a host, a promoter such as the lac, trp, tac, gal or ara promoter can be used.

Regarding a region contained in addition to the above-mentioned elements, the vector of the present invention may have, for example, a replication origin, a drug-resistance gene used as a selectable marker, or a regulatory sequence such as an operator or a terminator.

Operators that are present in expression-regulatory regions of various genes such as the lac operator derived from the *Escherichia coli* lactose operon can be used according to the present invention. A promoter can be allowed to act by canceling the function of the lac operator using an appropriate inducer such as lactose or an analog thereof (preferably, isopropyl-β-D-thiogalactoside (IPTG)). Such an operator sequence is usually placed downstream of a promoter and near a transcription initiation site.

The vector of the present invention may further have a regulatory gene necessary for a function of an operator (e.g., the lacI$^q$ gene for the lac operator).

It is possible to increase expression efficiency by including, downstream of a 5'-untranslated region, a nucleotide sequence complementary to an anti-downstream box sequence in ribosomal RNA of a host to be used, in addition to the above-mentioned elements. For example, in case of *Escherichia coli*, an anti-downstream box sequence is present from position 1467 to position 1481 in 16S ribosomal RNA (The EMBO Journal, 15:665–674 (1996)). It is possible to use a region encoding an N-terminal peptide of a cold shock protein which contains a nucleotide sequence highly complementary to this sequence. It is effective to place a sequence complementary to an anti-downstream box sequence such that it starts from around the first to fifteenth nucleotide from the initiation codon. A gene encoding a protein of interest can be incorporated into a vector such that the protein is expressed as a fusion protein with the N-terminal peptide. Alternatively, a base substitution may be introduced using a site directed mutagenesis method such that a gene encoding a protein of interest becomes complementary to an anti-downstream box sequence. If a gene encoding a protein of interest is incorporated into a vector such that the protein of interest is expressed as a fusion protein, the peptide may be of any length as long as the activity of the protein of interest is not abolished. The vector for expressing a fusion protein may be engineered, for example, at the joint site so that a protein of interest can be separated from the fusion protein using an appropriate protease. Alternatively, it may be engineered so that the fusion protein is expressed as a protein fused with a peptide that can be utilized for purification or detection. Examples of peptides that can be utilized for purification of expressed proteins include, but are not limited to, histidine tag (His-Tag) and glutathione-S-transferase (GST).

For example, a protein of interest is expressed using the vector of the present invention constructed as a plasmid as follows. A transformant for expressing the protein of interest can be obtained by cloning a gene encoding the protein into the plasmid vector of the present invention and transforming an appropriate host with the plasmid. The transformant specifically expresses the protein of interest by lowering the culture temperature. If the vector has an operator, the function of the operator may be canceled using an appropriate means to induce a promoter.

If the vector of the present invention is used for protein expression, a protein of interest is preferentially translated due to the above-mentioned LACE effect. As a result, the content of the protein of interest in a culture is high as compared with conventional expression of recombinant proteins and, therefore, it is possible to prepare the protein of interest with high purity. An isotope-labeled protein can be prepared by expressing a protein of interest in the presence of an appropriate isotope. The thus obtained highly pure labeled protein is suitable for structural analysis using NMR. For example, a culture or a lysate of a culture can be directly subjected to NMR analysis.

EXAMPLES

The following Examples illustrate the present invention in more detail, but are not to be construed to limit the scope thereof.

Among the procedures described herein, basic procedures including plasmid preparation and restriction enzyme digestion were carried out according to the methods as described in T. Maniatis et al. (eds.), Molecular Cloning: A Laboratory Manual 2nd ed. (1989) Cold Spring Harbor Laboratory. Unless otherwise noted, *Escherichia coli* JM109 was used as a host for the plasmid construction as described below, and LB medium (1% Tryptone, 0.5% yeast extract, 0.5% NaCl, pH 7.0) containing 50 µg/ml of ampicillin or LB agar medium prepared by adding agar at a concentration of 1.5% to the LB medium and solidifying the resulting mixture was used.

Referential Example

Construction of Plasmid pCold08NC2 pCold08NC2 was constructed based on the description of WO 99/27117 using, as a starting material, a plasmid pMM047 harbored in *Escherichia coli* JM109/pMM047 (FERM BP-6523) (deposited on Oct. 31, 1997 (date of original deposit) at International Patent Organism Depositary, National Institute of Advanced Science and Technology, AIST Tsukuba Central 6, 1—1, Higashi 1-Chome, Tsukuba, Ibaraki 305-8566, Japan). The plasmid pCold08NC2 has the following in this order from upstream to downstream: the lac promoter, a modified *Escherichia coli* cspA gene-derived 5'-UTR and a multiple cloning site. In addition, the plasmid has the lacI gene, a downstream box sequence that is completely complementary to an anti-downstream sequence in the *Escherichia coli* 16S ribosomal RNA, a histidine tag consisting of six histidine residues, and a nucleotide sequence encoding an amino acid sequence recognized by factor Xa.

Example 1

Construction of Vector pCold08s2 and Examination of Protein Expression Level (1) Construction of Plasmid Vector pCold08s2

An insertion mutation of 20 nucleotides was introduced as follows into the 5'-UTR-encoding portion in the plasmid pCold08NC2 from Referential Example 1.

A PCR was carried out using the plasmid pCold08NC2 as a template as well as a synthetic primer Sp20F (SEQ ID NO:6) and a primer CSPterR (SEQ ID NO:7). A reaction mixture containing 50 ng of pCold08NC2, 5 µl of Ex Taq buffer, 8 µl of dNTP mix, 5 pmol of the primer Sp20, 5 pmol of the primer CSPterR, 0.5 µl of Takara Ex Taq (Takara Bio) and sterile water to a total volume of 50 µl was subjected to a PCR (30 cycles of 94° C. for 1 minute (denaturation), 55° C. for 1 minute (primer annealing) and 72° C. for 1 minute (synthesis reaction)). The whole PCR reaction mixture was subjected to electrophoresis on 3% (w/v) low melting point agarose gel. An about 300-bp amplified DNA fragment was purified from the gel, suspended in 5 µl of sterile water and used as an amplified fragment SC.

A PCR was carried out under similar conditions using a synthetic primer Sp20R (SEQ ID NO:8) and a primer NheF2 (SEQ ID NO:9) as well as pCold08 as a template. The whole PCR reaction mixture was subjected to electrophoresis on 3% (w/v) low melting point agarose gel. An about 150-bp amplified DNA fragment was purified from the gel, suspended in 5 µl of sterile water and used as an amplified fragment SN.

A mixture containing 1 µl each of the amplified fragments SC and SN, 5 µl of Ex Taq buffer, 5 µl dNTP mix and sterile water to a total volume of 50 µl was heated at 94° C. for 10 minutes, cooled to 37° C. over 60 minutes and incubated at 37° C. for 15 minutes. 0.5 µl of Takara Ex Taq was added thereto, and the mixture was heated at 72° C. for 3 minutes.

5 pmol each of the primers NheF2 and CSPterR, 5 µl of Ex Taq buffer, 5 µl of dNTP mix and sterile water to a total volume of 100 µl were added to the reaction mixture. The resulting reaction mixture was subjected to a PCR (30 cycles of 94° C. for 1 minute, 55° C. for 1 minute and 72° C. for 2 minutes). The whole PCR reaction mixture was subjected to electrophoresis on 3% (w/v) low melting point agarose gel. An about 400-bp amplified DNA fragment was purified from the gel, suspended in 5 µl of sterile water and used as an amplified fragment Sp20-1.

Sp20-1 was doubly digested with restriction enzymes NheI and EcoRI (both from Takara Bio). The resulting DNA fragment was separated by electrophoresis on 1% low melting point agarose gel, and then extracted and purified. The purified DNA fragment and pCold08 digested with NheI and EcoRI were mixed and ligated together using DNA Ligation Kit (Takara Bio). The ligation reaction mixture was used to transform *Escherichia coli* JM109 and the transformants were grown on LB agar media containing ampicillin. Plasmids were prepared from the resulting colonies, and subjected to DNA sequencing. A plasmid into which the PCR product had been properly inserted was selected and designated as pCold08s2. In pCold08s2, a nucleotide sequence 5'-GAGCGGATAACAATTTCACA-3' (SEQ ID NO:10) is inserted between +120 and +121 in the 5'-UTR of pCold08NC2 (SEQ ID NO:5). The transcription initiation site in the lac operator is defined as +1. This position corresponds to the position between nucleotide 597 and nucleotide 598 of the nucleotide sequence of the cspA gene as shown in SEQ ID NO:1. The nucleotide sequence of the 5'-UTR contained in pCold08s2 is shown in SEQ ID NO:2.

(2) Construction of Plasmids for Expressing Proteins (2)-1 Construction of Plasmid Vector pCold08s2-GFP A gene encoding a GFP protein derived from *Aequorea victoria* was incorporated into pCold082 as follows. A PCR was carried out using a plasmid pQBI63 (Takara Bio) as a template as well as a synthetic primer GFP-F (SEQ ID NO:11) and a primer GFP-R (SEQ ID NO:12). A reaction mixture containing 50 ng of pQBI63, 5 µl of Ex Taq buffer, 8 µl of dNTP mix, 5 pmol each of the primers GFP-F and GFP-R, 0.5 µl of Takara Ex Taq (Takara Bio) and sterile water to a total volume of 50 µl was subjected to a PCR (30 cycles of 94° C. for 1 minute, 55° C. for 1 minute and 72° C. for 1 minute). The whole PCR reaction mixture was subjected to electrophoresis on 3% (w/v) low melting point agarose gel. An about 700-bp amplified DNA fragment containing the GFP gene was purified from the gel and suspended in 5 µl of sterile water. The DNA fragment was doubly digested with EcoRI and XbaI (Takara Bio). The digested DNA fragment was separated by electrophoresis on 1% low melting point agarose gel, and then extracted and purified. The purified DNA fragment and pCold08s2 digested with EcoRI and XbaI were mixed and ligated together using DNA Ligation Kit (Takara Bio). The ligation reaction mixture was used to transform *Escherichia coli* JM109 and the transformants were grown on LB agar media containing ampicillin. Plasmids were prepared from the resulting colonies, and subjected to DNA sequencing. A plasmid into which the PCR product had been properly inserted was selected and designated as pCold08s2-GFP. In addition, the amplified DNA fragment containing the GFP gene was incorporated into pCold08NC2, which does not have an inserted sequence in the 5'-UTR, in a similar manner to obtain pCold08-GFP.

(2)-2 Construction of Plasmid Vector pCold08s2-H296

A gene encoding the H296 fragment protein, which is a heparin-binding polypeptide derived from fibronectin, was incorporated into pCold082 as follows.

A PCR was carried out using a plasmid pCH102 (U.S. Pat. No. 5,198,423) as a template as well as a synthetic primer H296-F (SEQ ID NO:13) and a primer H296-R (SEQ ID NO:14). A reaction mixture containing 50 ng of pCH102, 5 µl of Ex Taq buffer, 8 µl of dNTP mix, 5 pmol each of the primers H296-F and H296-R, 0.5 µl of Takara Ex Taq and sterile water to a total volume of 50 µl was subjected to a PCR (30 cycles of 94° C. for 1 minute, 55° C. for 1 minute and 72° C. for 1 minute). The whole PCR reaction mixture was subjected to electrophoresis on 3% (w/v) low melting point agarose gel. An about 1-kbp amplified DNA fragment was purified from the gel and suspended in 5 μl of sterile water. The DNA fragment was doubly digested with EcoRI and BamHI (Takara Bio). The digested DNA fragment was separated by electrophoresis on 1% low melting point agarose gel, and then extracted and purified. The purified DNA fragment containing the H296 gene and pCold08s2 digested with EcoRI and BamHI were mixed and ligated together using DNA Ligation Kit (Takara Bio). The ligation reaction mixture was used to transform Escherichia coli JM109 and the transformants were grown on LB agar media containing ampicillin. Plasmids were prepared from the resulting colonies, and subjected to DNA sequencing. A plasmid into which the PCR product had been properly inserted was selected and designated as pCold08s2-H296. In addition, the amplified DNA fragment containing the H296 gene was incorporated into pCold08NC2, which does not have an inserted sequence in the 5'-UTR, in a similar manner to obtain pCold08-H296.

(2)-3 Construction of Plasmid Vector pCold08s2-lac

A plasmid pKM005 which contains the β-galactosidase (lacZ) gene (M. Inouye (ed.), Experimental Manipulation of Gene Expression, pp. 15–32, 1983, New York Academic Press) was digested with BamHI and SalI (Takara Bio). The reaction mixture was subjected to electrophoresis on 1% (w/v) low melting point agarose gel. A DNA fragment containing the lacZ gene was purified from the gel and suspended in 5 μl of sterile water. The purified DNA fragment and pCold08s2 digested with BamHI and SalI were mixed and ligated together using DNA Ligation Kit (Takara Bio). 10 μl of the ligation reaction mixture was used to transform Escherichia coli JM109, and the transformants were grown on LB agar media containing ampicillin. Plasmids were prepared from the resulting colonies, and subjected to DNA sequencing. A plasmid into which the PCR product had been properly inserted was selected and designated as pCold08s2-lac. In addition, the amplified DNA fragment containing the lacZ gene was incorporated into pCold08NC2, which does not have an inserted sequence in the 5'-UTR, in a similar manner to obtain pCold08-lac.

(3) Assessment of Expression Levels (3)-1 Assessment of Expression Levels Using pCold08s2-GFP and pCold08s2-H296

Escherichia coli BL21 (Novagen) or CL83 (J. Bacteriol., 180:90–95 (1998)) was transformed with pCold08s2-GFP (prepared in Example 1-(2)-1) or pCold08s2-H296 (prepared in Example 1-(2)-2), or pCold08-GFP or pCold08-H296 as a control. Each transformant was inoculated into 2.5 ml of LB medium containing 50 μg/ml of ampicillin and cultured overnight at 37° C. with shaking. The culture was inoculated into 3 ml of the same medium at a concentration of 1% (v/v) and cultured at 37° C. with shaking. When the turbidity (OD600 nm) reached 0.2, the culture temperature was lowered to 15° C., and incubation was continued at the temperature for 15 minutes. Then, IPTG was added thereto at a final concentration of 1 mM, and cultivation with shaking was continued for 24 hours while maintaining the culture temperature at 15° C. After measuring the turbidity (OD 600 nm), cells collected from 2 ml of the culture by centrifugation were suspended in 100 μl of a cell suspension solution (50 mM tris-hydrochloride buffer (pH 7.5), 150 mM sodium chloride). The suspension corresponding to about $3.75 \times 10^6$ cells (calculated based on the turbidity) was subjected to electrophoresis on 10% SDS polyacrylamide gel. The gel was stained with Coomassie Brilliant Blue (CBB) and then decolorized. SDS polyacrylamide gel electrophoresis was carried out as described in "Seibutsukagaku Jikken No Tebiki 2" (Kagakudojin). The gel was subjected to image analysis using Total Lab ver.1.11 (Nonlinear Dynamics) to quantify the expression levels of GFP and H296. Ratios of the determined protein expression levels for recombinants harboring pCold08s2-GFP and pCold08s2-H296 to those for recombinants harboring pCold08-GFP and pCold08-H296, which do not have insertion in the 5'-UTRs, are shown in Table 1.

TABLE 1

| Plasmid | Host | Expression rate* |
| --- | --- | --- |
| pCold08s2-GFP | BL21 | 1.5-fold |
|  | CL83 | 2.0-fold |
| pCold08s2-H296 | BL21 | 1.5-fold |
|  | CL83 | 1.5-fold |

*Expression rate: expression level for pCold08s2 clone/expression level for pCold08 clone, calculated based on results of image analyses.

Based on the results of SDS polyacrylamide gel analyses as shown in Table 1, expression levels for the clones prepared using the vector pCold08s2, which has insertion of 20 nucleotides in the 5'-UTR, were higher than those for the clones prepared using pCold08NC2.

(3)-2 Assessment of Expression Level Using pCold08s2-lac

Escherichia coli BL21 or CL83 was transformed with pCold08s2-lac (prepared in Example 1-(2)-3), or pCold08-lac as a control. Each transformant was inoculated into 2.5 ml of LB medium containing 50 μg/ml of ampicillin and cultured overnight at 37° C. with shaking. The culture was inoculated into 3 ml of the same medium at a concentration of 1% (v/v) and cultured at 37° C. with shaking. When the turbidity (OD 600 nm) reached 0.2, a sample was taken from the culture, the culture temperature was lowered to 15° C., and incubation was continued at the temperature for 15 minutes. Then, IPTG was added thereto at a final concentration of 1 mM to induce the expression, and cultivation was continued while maintaining the culture temperature at 15° C. Samples taken from the culture at 37° C. just before the induction and the culture 3 or 24 hours after the induction were subjected to β-galactosidase activity measurements according to the method as described in J. H. Miller, Experiments in Molecular Genetics, pp.352–355, 1972, Cold Spring Harbor Laboratory. The results are shown in Table 2.

TABLE 2

| | | β-Galactosidase activity (unit) | | |
| --- | --- | --- | --- | --- |
| Plasmid | Host | Before induction | 3 hours after induction | 24 hours after induction |
| pCold08-lac | BL21 | 10110 | 49510 | 85550 |
|  | CL83 | 6971 | 28514 | 31504 |
| pCold08s2-lac | BL21 | 9151 | 66314 | 119770 |
|  | CL83 | 5172 | 56028 | 72459 |

As shown in Table 2, the transformant harboring pCold08s2-lac, which has insertion of 20 nucleotides in the 5'-UTR, had a β-galactosidase activity higher than the transformant harboring pCold08-lac (1.4-fold (host: BL21) or 2.3-fold (host: CL83)) 24 hours after the induction.

Example 2

Construction of Vectors pCold08s12 and pCold08s32 and Examination of Protein Expression Levels (1) Construction of Plasmid Vector pCold08s12

A plasmid pCold08s12 was constructed as described in Example 1-(1) except that primers Sp12F (SEQ ID NO:15) and Sp12R (SEQ ID NO:16) were used in place of the primers Sp20F and CSPterR. In the plasmid pCold08s12, an insertion mutation of 12 nucleotides is introduced in the 5'-UTR-encoding portion in the plasmid pCold08NC2 from Referential Example 1.

In pCold08s12, a nucleotide sequence 5'-ATGTTTTG-TAGA-3' (SEQ ID NO:17) is inserted between +120 and +121 of the 5'-UTR in pCold08NC2 (SEQ ID NO:5). The nucleotide sequence of the 5-UTR contained in pCold08s12 is shown in SEQ ID NO:3.

(2) Construction of Plasmid Vector pCold08s32

A plasmid pCold08s32 was constructed as described in Example 1-(1) except that primers Sp32F (SEQ ID NO:18) and Sp32R (SEQ ID NO:19) were used in place of the primers Sp20F and Sp20R. In the plasmid pCold08s32, an insertion mutation of 32 nucleotides is introduced in the 5'-UTR-encoding portion in the plasmid pCold08NC2 from Referential Example 1.

In pCold08s32, a nucleotide sequence 5'-ATGTTTTGTA-GATTTGAAAGAGTAGATTAGTA-3' (SEQ ID NO:20) is inserted between +120 and +121 of the 5'-UTR in pCold08NC2 (SEQ ID NO:5) The nucleotide sequence of the 5'-UTR contained in pCold08s32 is shown in SEQ ID NO:4.

(3) Construction of Plasmid Vectors pCold08s12-H296 and pCold08s32-H296

An about 1-kbp DNA fragment containing the H296 gene prepared as described in Example 1-(2)-1 was doubly digested with EcoRI and BamHI. The digested DNA fragment was separated by electrophoresis on 1% low melting point agarose gel, and then extracted and purified. The purified DNA fragment and pCold08s12 or pCold08s32 digested with EcoRI and BamHI were mixed and ligated together using DNA Ligation Kit (Takara Bio). The ligation reaction mixture was used to transform *Escherichia coli* JM109, and the transformants were grown on LB agar media containing ampicillin. Plasmids were prepared from the resulting colonies, and subjected to DNA sequencing. Plasmids into which the PCR product had been properly inserted were selected and designated as pCold08s12-H296 and pCold08s32-H296.

(4) Assessment of Expression Levels Using pCold08s12-H296 and pCold08s32-H296

*Escherichia coli* BL21 or CL83 was transformed with pCold08s12-H296 or pCold08s32-H296 prepared in (3) above, or pCold08-H296 as a control. Each transformant was inoculated into 2.5 ml of LB medium containing 50 μg/ml of ampicillin and cultured overnight at 37° C. with shaking. The culture was inoculated into 3 ml of the same medium at a concentration of 1% (v/v) and cultured at 37° C. with shaking. When the turbidity (OD 600 nm) reached 0.2, the culture temperature was lowered to 15° C., and incubation was continued at the temperature for 15 minutes. Then, IPTG was added thereto at a final concentration of 1 mM, and cultivation with shaking was continued for 24 hours while maintaining the culture temperature at 15° C. The expression levels of H296 for the respective recombinants were quantified for the resulting cultures as described in Example 1-(3)-1. Ratios of the determined protein expression levels for recombinants harboring pCold08s12-H296 and pCold08s32-H296 to that for a recombinant harboring pCold08-H296, which does not have insertion in the 5'-UTR, are shown in Table 3.

TABLE 3

| Plasmid | Host | Expression rate* |
|---|---|---|
| pCold08s12-H296 | BL21 | 1.3-fold |
| | CL83 | 1.5-fold |
| pCold08s32-H296 | BL21 | 1.4-fold |
| | CL83 | 1.8-fold |

*Expression rate: expression level for pCold08s12 or pColds32 clone/expression level for pCold08 clone, calculated based on results of image analyses.

The results of SDS polyacrylamide gel analyses proved that the expression levels observed using the vectors having the 5'-UTR with inserted 12 or 32 nucleotides were increased as compared with the expression level observed using the vector without the insertion.

INDUSTRIAL APPLICABILITY

The present invention provides an expression vector that results in high expression efficiency under low-temperature conditions. It is possible to specifically express a protein of interest to prepare a highly pure protein preparation using the vector. In addition, it is possible to efficiently obtain a protein retaining its activity by expressing the protein under low-temperature conditions utilizing the vector.

Sequence Listing Free Text

SEQ ID NO:2: Modified 5' Untranslated Region of cspA Gene

SEQ ID NO:3: Modified 5' Untranslated Region of cspA Gene

SEQ ID NO:4: Modified 5' Untranslated Region of cspA Gene

SEQ ID NO:5: Modified 5' Untranslated Region of cspA Gene

SEQ ID NO:6: Synthetic Primer for PCR

SEQ ID NO:7: Synthetic Primer for PCR

SEQ ID NO:8: Synthetic Primer for PCR

SEQ ID NO:9: Synthetic Primer for PCR

SEQ ID NO:10: Synthetic Nucleotide inserted into 5' Untranslated Region of cspA Gene SEQ ID NO:11: Synthetic Primer for PCR SEQ ID NO:12: Synthetic Primer for PCR SEQ ID NO:13: Synthetic Primer for PCR SEQ ID NO:14: Synthetic Primer for PCR SEQ ID NO:15: Synthetic Primer for PCR SEQ ID NO:16: Synthetic Primer for PCR SEQ ID NO:17: Synthetic Nucleotide inserted into 5' Untranslated Region of cspA Gene SEQ ID NO:18: Synthetic Primer for PCR SEQ ID NO:19: Synthetic Primer for PCR SEQ ID NO:20: Synthetic Nucleotide inserted into 5' Untranslated Region of cspA Gene

The invention claimed is:

1. A vector having a portion encoding a 5'-untranslated region from an mRNA for a cold shock protein gene, wherein a mutation is introduced into the 5'-untranslated region such that a distance between stem structures formed in said region is altered and wherein said introduced mutation is an insertion or deletion of a nucleotide, introduced into the region of SEQ ID NO:1 corresponding to nucleotide 593 to nucleotide 598.

2. The vector according to claim 1, wherein the portion encoding a 5'-untranslated region further has an operator.

3. The vector according to claim 1, which has a promoter located upstream of the portion encoding a 5'-untranslated region.

4. The vector according to claim 1, which has a nucleotide sequence that is complementary to an anti-downstream box sequence in a ribosomal RNA of a host to be used, wherein said nucleotide sequence is located downstream of the portion encoding a 5'-untranslated region.

5. The vector according to claim 1, which is a plasmid vector.

6. The vector according to claim 2, wherein the portion encoding a 5'-untranslated region is a portion encoding a 5'-untranslated region that has the nucleotide sequence of SEQ ID NO:2, 3 or 4.

7. A method for expressing a protein of interest, the method comprising:
   (1) transforming a host with the vector defined by any one of claims 1 and 2, 3, 4, 5, 6 into which a gene encoding a protein of interest has been incorporated to obtain a transformant;
   (2) culturing the transformant; and
   (3) shifting the culture temperature down to a temperature lower than a conventional culture temperature to express the protein of interest.

8. The method according to claim 7, wherein a promoter is induced during or after step (3).

\* \* \* \* \*

SEQUENCE LISTING

<160> NUMBER OF SEQ ID NOS: 20

<210> SEQ ID NO 1
<211> LENGTH: 1209
<212> TYPE: DNA
<213> ORGANISM: Escherichia coli

<400> SEQUENCE: 1

```
aagcttcgat gcaattcacg atcccgcagt gtgatttgag gagttttcaa tggaatataa      60
agatccaatg catgagctgt tgagcagcct ggaacagatt gtttttaaag atgaaacgca     120
gaaaattacc ctgacgcaca gaacaacgtc ctgtaccgaa attgagcagt tacgaaaagg     180
gacaggatta aaaatcgatg atttcgcccg ggttttgggc gtatcagtcg ccatggtaaa     240
ggaatgggaa tccagacgcg tgaagccttc aagtgccgaa ctaaaattga tgcgtttgat     300
tcaagccaac ccggcattaa gtaagcagtt gatggaatag acttttatcc actttattgc     360
tgtttacggt cctgatgaca ggaccgtttt ccaaccgatt aatcataaat atgaaaaata     420
attgttgcat cacccgccaa tgcgtggctt aatgcacatc aacggtttga cgtacagacc     480
attaaagcag tgtagtaagg caagtcccct caagagttat cgttgatacc cctcgtagtg     540
cacattcctt taacgcttca aaatctgtaa agcacgccat atcgccgaaa ggcacactta     600
attattaaag gtaatacact atgtccggta aaatgactgg tatcgtaaaa tggttcaacg     660
ctgacaaagg cttcggcttc atcactcctg acgatggctc taaagatgtg ttcgtacact     720
tctctgctat ccagaacgat ggttacaaat ctctggacga aggtcagaaa gtgtccttca     780
ccatcgaaaa cggcgctaaa ggcccggcag ctggtaacgt aaccagcctg taatctctgc     840
ttaaaagcac agaatctaag atccctgcca tttggcgggg attttttat tgttttcag      900
gaaataaata atcgatcgcg taataaaatc tattattatt tttgtgaaga ataaatttgg     960
gtgcaatgag aatgcgcaac gccgtaagta aggcgggaat aatttcccgc cgaagactct    1020
tactctttca atttgcaggc taaaaacgcc gccagctcat aactctcctg tttaatatgc    1080
aattcacaca gtgaatctct tatcatccag gtgaaaaata aaagcgtgaa acaaatcact    1140
attaaagaaa gtaatctata tttctgcgca ttccagctct gtgttgattt cacgagtatg    1200
tactgcacc                                                            1209
```

<210> SEQ ID NO 2
<211> LENGTH: 164
<212> TYPE: DNA
<213> ORGANISM: Artificial Sequence
<220> FEATURE:
<223> OTHER INFORMATION: Modified 5' Untranslated Region of cspA Gene

<400> SEQUENCE: 2

```
aaattgtgag cggataacaa tttgatgtgc tagcgcatat ccagtgtagt aaggcaagtc      60
ccttcaagag cctttaacgc ttcaaaatct gtaaagcacg ccatatcgcc gaaaggcaca     120
cgagcggata acaatttcac attaattatt aaaggtaata cacc                      164
```

<210> SEQ ID NO 3
<211> LENGTH: 156
<212> TYPE: DNA
<213> ORGANISM: Artificial Sequence
<220> FEATURE:
<223> OTHER INFORMATION: Modified 5' Untranslated Region of cspA Gene

<400> SEQUENCE: 3

```
aaattgtgag cggataacaa tttgatgtgc tagcgcatat ccagtgtagt aaggcaagtc    60
ccttcaagag cctttaacgc ttcaaaatct gtaaagcacg ccatatcgcc gaaaggcaca   120
catgttttgt agattaatta ttaaaggtaa tacacc                             156

<210> SEQ ID NO 4
<211> LENGTH: 176
<212> TYPE: DNA
<213> ORGANISM: Artificial Sequence
<220> FEATURE:
<223> OTHER INFORMATION: Modified 5' Untranslated Region of cspA Gene

<400> SEQUENCE: 4
aaattgtgag cggataacaa tttgatgtgc tagcgcatat ccagtgtagt aaggcaagtc    60
ccttcaagag cctttaacgc ttcaaaatct gtaaagcacg ccatatcgcc gaaaggcaca   120
catgttttgt agatttgaaa gagtagatta gtattaatta ttaaaggtaa tacacc       176

<210> SEQ ID NO 5
<211> LENGTH: 144
<212> TYPE: DNA
<213> ORGANISM: Artificial Sequence
<220> FEATURE:
<223> OTHER INFORMATION: Modified 5' Untranslated Region of cspA Gene

<400> SEQUENCE: 5
aaattgtgag cggataacaa tttgatgtgc tagcgcatat ccagtgtagt aaggcaagtc    60
ccttcaagag cctttaacgc ttcaaaatct gtaaagcacg ccatatcgcc gaaaggcaca   120
cttaattatt aaaggtaata cacc                                          144

<210> SEQ ID NO 6
<211> LENGTH: 40
<212> TYPE: DNA
<213> ORGANISM: Artificial Sequence
<220> FEATURE:
<223> OTHER INFORMATION: Synthetic Primer for PCR

<400> SEQUENCE: 6
gtgcggataa caatttcaca ttaattatta aggtaatac                           40

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer for PCR

<400> SEQUENCE: 7
tgcgcattct cattgcaccc                                                20

<210> SEQ ID NO 8
<211> LENGTH: 40
<212> TYPE: DNA
<213> ORGANISM: Artificial Sequence
<220> FEATURE:
<223> OTHER INFORMATION: Synthetic Primer for PCR

<400> SEQUENCE: 8
tgtgaaattg ttatccgctc gtgtgccttt cggcgatatg                          40

<210> SEQ ID NO 9
<211> LENGTH: 31
<212> TYPE: DNA
```

<213> ORGANISM: Artificial Sequence
<220> FEATURE:
<223> OTHER INFORMATION: Synthetic Primer for PCR

<400> SEQUENCE: 9
gttttcccgc tagccaaatt gtgagcggat a        31

<210> SEQ ID NO 10
<211> LENGTH: 20
<212> TYPE: DNA
<213> ORGANISM: Artificial Sequence
<220> FEATURE:
<223> OTHER INFORMATION: Synthetic Nucleotide inserted into 5'
      Untranslated Region of cspA Gene

<400> SEQUENCE: 10
gagcggataa caatttcaca        20

<210> SEQ ID NO 11
<211> LENGTH: 38
<212> TYPE: DNA
<213> ORGANISM: Artificial Sequence
<220> FEATURE:
<223> OTHER INFORMATION: Synthetic Primer for PCR

<400> SEQUENCE: 11
aagataacaa aggaattcga gtaaaggaga agaacttt        38

<210> SEQ ID NO 12
<211> LENGTH: 37
<212> TYPE: DNA
<213> ORGANISM: Artificial Sequence
<220> FEATURE:
<223> OTHER INFORMATION: Synthetic Primer for PCR

<400> SEQUENCE: 12
tctggacatt ctagattatt tgtatagttc atccatg        37

<210> SEQ ID NO 13
<211> LENGTH: 36
<212> TYPE: DNA
<213> ORGANISM: Artificial Sequence
<220> FEATURE:
<223> OTHER INFORMATION: Synthetic Primer for PCR

<400> SEQUENCE: 13
ccatccatgg aattcggcta ttcctgcacc aactga        36

<210> SEQ ID NO 14
<211> LENGTH: 36
<212> TYPE: DNA
<213> ORGANISM: Artificial Sequence
<220> FEATURE:
<223> OTHER INFORMATION: Synthetic Primer for PCR

<400> SEQUENCE: 14
gaaaacctag gatccttatg tggaaggaac atccaa        36

<210> SEQ ID NO 15
<211> LENGTH: 52
<212> TYPE: DNA
<213> ORGANISM: Artificial Sequence
<220> FEATURE:
<223> OTHER INFORMATION: Synthetic Primer for PCR

<400> SEQUENCE: 15

```
catatcgccg aaaggcacac atgttttgta gattaattat taaaggtaat ac            52

<210> SEQ ID NO 16
<211> LENGTH: 52
<212> TYPE: DNA
<213> ORGANISM: Artificial Sequence
<220> FEATURE:
<223> OTHER INFORMATION: Synthetic Primer for PCR

<400> SEQUENCE: 16
gtattacctt taataattaa tctacaaaac atgtgtgcct ttcggcgata tg            52

<210> SEQ ID NO 17
<211> LENGTH: 12
<212> TYPE: DNA
<213> ORGANISM: Artificial Sequence
<220> FEATURE:
<223> OTHER INFORMATION: Synthetic Nucleotide inserted into 5'
      Untranslated Region of cspA Gene

<400> SEQUENCE: 17
atgttttgta ga                                                        12

<210> SEQ ID NO 18
<211> LENGTH: 52
<212> TYPE: DNA
<213> ORGANISM: Artificial Sequence
<220> FEATURE:
<223> OTHER INFORMATION: Synthetic Primer for PCR

<400> SEQUENCE: 18
atgttttgta gatttgaaag agtagattag tattaattat taaaggtaat ac            52

<210> SEQ ID NO 19
<211> LENGTH: 52
<212> TYPE: DNA
<213> ORGANISM: Artificial Sequence
<220> FEATURE:
<223> OTHER INFORMATION: Synthetic Primer for PCR

<400> SEQUENCE: 19
tactaatcta ctctttcaaa tctacaaaac atgtgtgcct ttcggcgata tg            52

<210> SEQ ID NO 20
<211> LENGTH: 32
<212> TYPE: DNA
<213> ORGANISM: Artificial Sequence
<220> FEATURE:
<223> OTHER INFORMATION: Synthetic Nucleotide inserted into 5'
      Untranslated Region of cspA Gene

<400> SEQUENCE: 20
atgttttgta gatttgaaag agtagattag ta                                  32
```